United States Patent
Nishimura et al.

(10) Patent No.: US 10,491,873 B2
(45) Date of Patent: Nov. 26, 2019

(54) SCANNING OBSERVATION APPARATUS AND IMAGE DISPLAY METHOD OF SCANNING OBSERVATION APPARATUS

(71) Applicant: OLYMPUS CORPORATION, Tokyo (JP)

(72) Inventors: Junichi Nishimura, Tokyo (JP); Atsuyoshi Shimamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 155 days.

(21) Appl. No.: 15/705,503

(22) Filed: Sep. 15, 2017

(65) Prior Publication Data
US 2018/0007335 A1    Jan. 4, 2018

Related U.S. Application Data

(63) Continuation of application No. PCT/JP2015/001665, filed on Mar. 24, 2015.

(51) Int. Cl.
*G02B 23/24* (2006.01)
*A61B 1/00* (2006.01)
(Continued)

(52) U.S. Cl.
CPC .......... *H04N 9/73* (2013.01); *A61B 1/00006* (2013.01); *A61B 1/00009* (2013.01);
(Continued)

(58) Field of Classification Search
CPC ................ H04N 9/73; H04N 5/23229; H04N 2005/2255; H04N 5/2251; H04N 5/2256;
(Continued)

(56) References Cited

U.S. PATENT DOCUMENTS

2008/0165360 A1*  7/2008  Johnston ............ A61B 1/00057
                                                                    356/394
2012/0215066 A1*  8/2012  Akiyama ........... A61B 1/00009
                                                                    600/109

FOREIGN PATENT DOCUMENTS

JP    2007-44221 A     2/2007
JP    2013-106899 A    6/2013
(Continued)

OTHER PUBLICATIONS

Japanese Office Action dated Jan. 8, 2019 in Japanese Patent Application No. 2017-507107.
(Continued)

*Primary Examiner* — Pankaj Kumar
*Assistant Examiner* — Alazar Tilahun
(74) *Attorney, Agent, or Firm* — Scully, Scott, Murphy & Presser, P.C.

(57) ABSTRACT

A scanning observation apparatus (10) deflects illumination light with an actuator (25) through an illumination optical system (26) to scan an object (32), subjects light from the object (32) to photoelectric conversion with an optical detector (44), performs processing with an image processor (46), and displays an image of the object (32) on a display (60). A memory (35) stores information on optical characteristics related to chromatic aberration of magnification of the illumination optical system (26) relative to light of predetermined colors. A scanning pattern calculator (45) calculates a scanning pattern, on the object (32), of light of each color using the information. Using the scanning pattern, the image processor (46) calibrates a plot position yielded by a photoelectric conversion signal from the optical detector (44) for light of each color and generates an image of the object (32), thereby more easily correcting the chromatic aberration of magnification.

7 Claims, 7 Drawing Sheets

(51) Int. Cl.
   *A61B 34/20* (2016.01)
   *H04N 5/232* (2006.01)
   *H04N 9/73* (2006.01)
   *G02B 26/10* (2006.01)
   *A61B 1/04* (2006.01)
   *A61B 1/06* (2006.01)
   *A61B 1/07* (2006.01)

(52) U.S. Cl.
   CPC .......... *A61B 1/00172* (2013.01); *A61B 1/042* (2013.01); *A61B 1/0638* (2013.01); *A61B 1/0669* (2013.01); *A61B 1/07* (2013.01); *G02B 23/2469* (2013.01); *G02B 26/103* (2013.01); *H04N 5/23229* (2013.01)

(58) Field of Classification Search
   CPC ............. H04N 5/23209; H04N 5/2351; H04N 5/2354; H04N 5/335; H04N 9/045; G02B 23/2469; G02B 26/103; G02B 23/2438; G02B 23/2423; A61B 1/0638; A61B 1/042; A61B 1/00172; A61B 1/0669; A61B 1/00006; A61B 1/07; A61B 1/00009; A61B 1/04; A61B 1/05; A61B 1/00188; A61B 1/00045
   USPC .......................................................... 348/67
   See application file for complete search history.

(56) References Cited

FOREIGN PATENT DOCUMENTS

| | | |
|---|---|---|
| JP | 5490331 B1 | 3/2014 |
| JP | 2015-22161 A | 2/2015 |
| WO | 2013/089053 A1 | 6/2013 |

OTHER PUBLICATIONS

International Preliminary Report on Patentability together with the Written Opinion from related International Application No. PCT/JP2015/001665 dated Oct. 5, 2017.
International Search Report dated Jun. 9, 2015 received in International Application No. PCT/JP2015/001665, together with an English-language translation.
Chinese Office Action dated Aug. 2, 2018 in Chinese Patent Application No. 201580077799.7.
Chinese Office Action dated Mar. 25, 2019 in Chinese Patent Application No. 201580077799.7.

\* cited by examiner

SCANNING OBSERVATION APPARATUS AND IMAGE DISPLAY METHOD OF SCANNING OBSERVATION APPARATUS

CROSS-REFERENCE TO RELATED APPLICATION

The present application is a Continuing Application based on International Application PCT/JP2015/001665 filed on Mar. 24, 2015, the content of which is incorporated herein by reference.

TECHNICAL FIELD

This disclosure relates to a scanning observation apparatus and an image display method of a scanning observation apparatus.

BACKGROUND

A known example of a scanning observation apparatus is a scanning endoscope apparatus that scans a test site by irradiating the test site with illumination light. The illumination light is emitted from an optical fiber extending through a scope and passes through an illumination optical system. The scanning endoscope apparatus scans while displacing the emission end of the optical fiber with an actuator and deflecting the illumination light, detects light reflected at the test site, and displays an image (for example, see JP 5490331 B2 (PTL 1)).

This scanning endoscope apparatus acquires coordinate information of the scanning pattern of light of a predetermined color using a light irradiation coordinate detection module, such as a Position Sensitive Detector (PSD), provided with a coordinate information acquisition function. The scanning endoscope apparatus also stores information on optical characteristics that, using the light of the predetermined color as a reference, indicate the correspondence relationship between the image height and amount of aberration of light of another color. When using the coordinate information to detect that the light of the predetermined color has been irradiated on a position of the test site corresponding to a predetermined image height, the scanning endoscope apparatus detects the amount of aberration of the light of the other color at the predetermined image height using the information on optical characteristics. The scanning endoscope apparatus then acquires image correction information for correcting the chromatic aberration of magnification of the image generated in accordance with reflected light from the light of the other color, performs image correction processing on the basis of the image correction information, and displays an image of the test site.

CITATION LIST

Patent Literature

PTL 1: JP 5490331 B2

SUMMARY

A scanning observation apparatus according to this disclosure deflects illumination light with an actuator through an illumination optical system to scan an object being illuminated, subjects light from the object being illuminated to photoelectric conversion with an optical detector, performs processing with an image processor, and displays an image of the object being illuminated on a display, the scanning observation apparatus comprising:

a memory configured to store information on optical characteristics related to a chromatic aberration of magnification of the illumination optical system relative to light of a plurality of predetermined colors; and a scanning pattern calculator configured to calculate a scanning pattern, on the object being illuminated, of the light of each color by referring to the information on optical characteristics; wherein by referring to the scanning pattern, the image processor calibrates a plot position yielded by a photoelectric conversion signal from the optical detector for the light of each color and generates an image of the object being illuminated.

As the information on optical characteristics, the memory may store information expressed as a third order or higher polynomial equation or a trigonometric function, or an expansion or conversion formula of the polynomial equation or the trigonometric function, representing a relationship between an amount of deflection h of the illumination light and a scanning angle $\theta\lambda$ of the light of each color relative to an optical axis of the illumination optical system, and for the light of each color, the scanning pattern calculator may calculate an irradiation position h' serving as the scanning pattern from the equation h'=z·tan $\theta\lambda$ by referring to the information on optical characteristics, where z is a distance from the illumination optical system to the object being illuminated.

As the information on optical characteristics, the memory may store information expressed as $h = a_4\theta\lambda^4 + a_3\theta\lambda^3 + a_2\theta\lambda^2 + a_1\theta\lambda^1 + a_0$, where $a_4$, $a_3$, $a_2$, $a_1$, and $a_0$ are coefficients, or $\theta\lambda = b_4 h^4 + b_3 h^3 + b_2 h^2 + b_1 h + b_0$, where $b_4$, $b_3$, $b_2$, $b_1$, and $b_0$ are coefficients.

As the information on optical characteristics, the memory may store information expressed as $h = f \cdot \sin\theta\lambda$, where f is a focal length of the illumination optical system.

The focal length f may be an actual measured value.

The object being illuminated may be scanned in a spiral centered on an optical axis of the illumination optical system; and the image processor may perform different image processing on an outermost area of the image of the object being illuminated than on another area.

The scanning observation apparatus may further comprise an optical fiber configured to guide the illumination light; and the actuator may displace an emission end of the optical fiber to deflect the illumination light emitted from the optical fiber.

An image display method according to this disclosure is for a scanning observation apparatus that deflects illumination light with an actuator through an illumination optical system to scan an object being illuminated, subjects light from the object being illuminated to photoelectric conversion with an optical detector, performs processing with an image processor, and displays an image of the object being illuminated on a display, the image display method comprising:

calculating, using a scanning pattern calculator, a scanning pattern on the object being illuminated by referring to information on optical characteristics stored in a memory and related to a chromatic aberration of magnification of the illumination optical system relative to light of a plurality of predetermined colors, the scanning pattern being calculated for the light of each color; and calibrating, using the image processor, a plot position by referring to the scanning pattern, the plot position being yielded by a photoelectric conversion signal from the optical detector for the light of each color, and generating an image of the object being illuminated.

DETAILED DESCRIPTION

The following describes embodiments of this disclosure with reference to the drawings.

Figure 1:
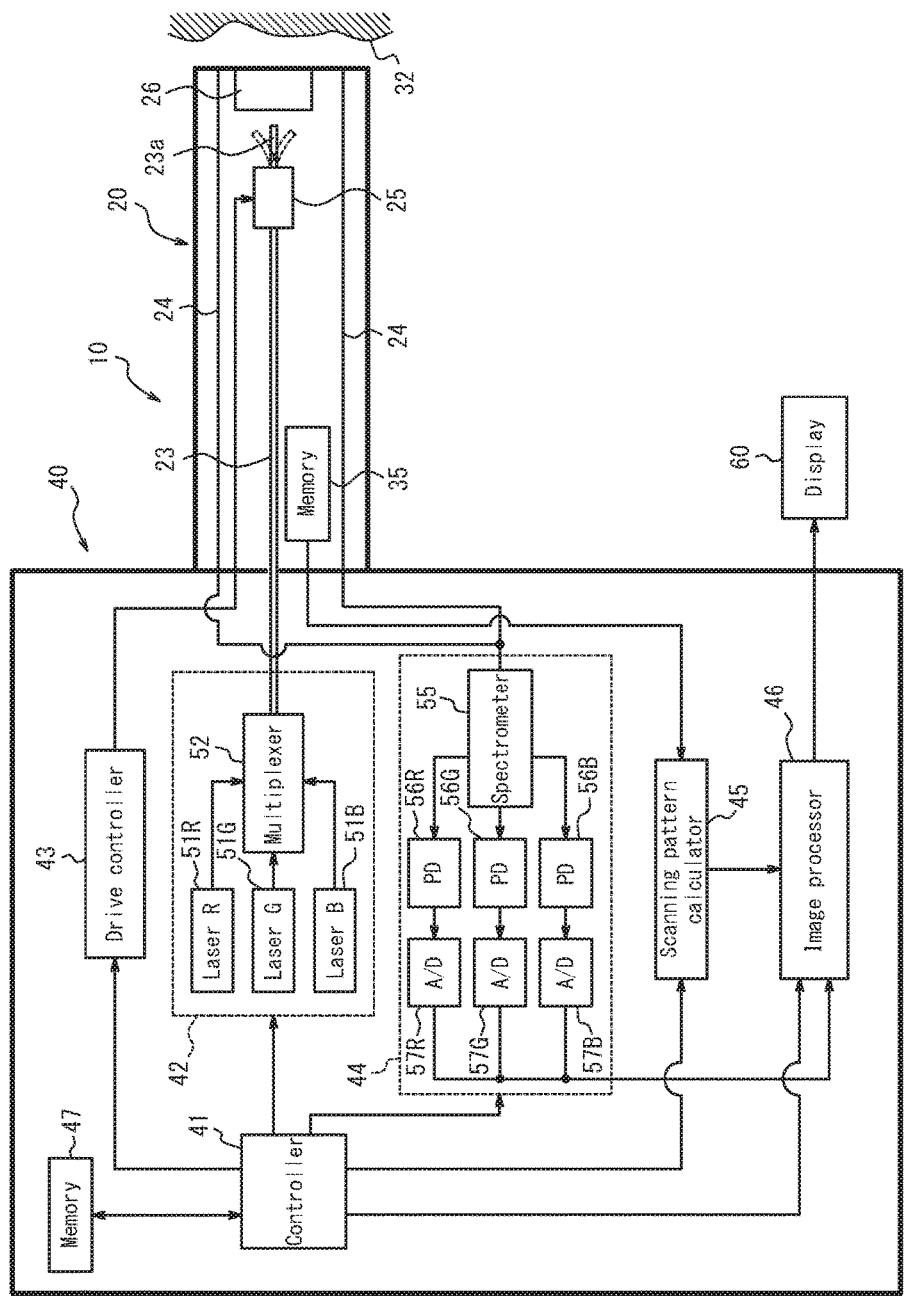
FIG. 1 is a block diagram schematically illustrating the main configuration of a scanning endoscope apparatus according to one of the disclosed embodiments.

FIG. 1 is a block diagram schematically illustrating the main configuration of a scanning endoscope apparatus according to one of the disclosed embodiments. The scanning endoscope apparatus 10 according to this embodiment includes a scope (endoscope) 20, an apparatus body 40, and a display 60.

Figure 2:
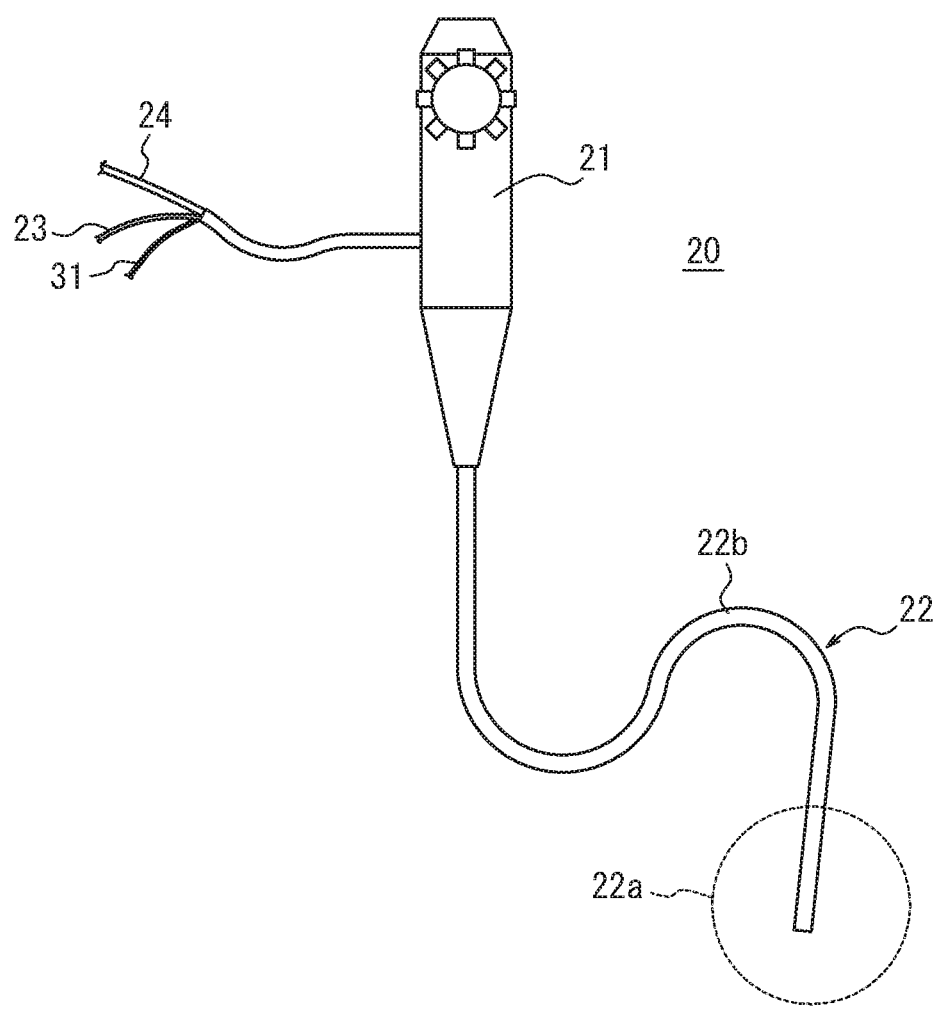
FIG. 2 is a schematic overview of the scope in FIG. 1.

The scope 20 is detachably connected to the apparatus body 40 by a connector or the like. The scope 20 includes an operation part 21 and an insertion part 22 as illustrated by the schematic view in FIG. 2. An optical fiber 23 for illumination and a fiber bundle 24 for detection are disposed inside the scope 20, extending from a base end joined to the apparatus body 40 to a tip 22a of the insertion part 22 (the portion indicated by the dashed circle in FIG. 2). Illumination light from the apparatus body 40 can enter the optical fiber 23 for illumination while the scope 20 is connected to the apparatus body 40. In the insertion part 22, the tip 22a is a hard portion that does not bend, whereas the portion excluding the tip 22a is a flexible portion 22b that does bend.

Figure 3:
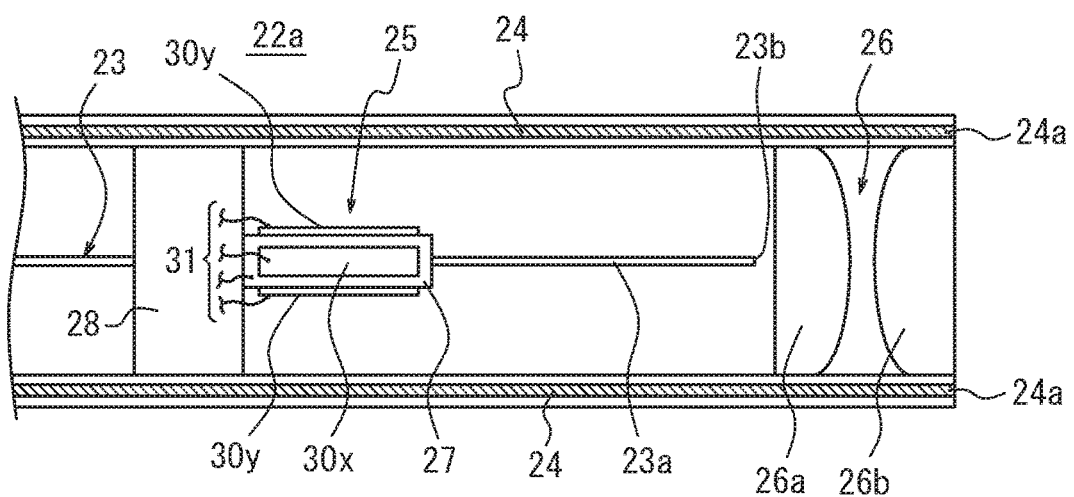
FIG. 3 is a cross-sectional diagram illustrating an enlargement of the tip of the scope in FIG. 2.

As illustrated in the partially expanded cross-sectional diagram of FIG. 3, an actuator 25 and an illumination optical system 26 are mounted in the tip 22a of the scope 20. The actuator 25 includes a ferrule 27 that holds an emission end 23a of the optical fiber 23 for illumination by the emission end 23a passing through the ferrule 27. The optical fiber 23 for illumination is adhered to the ferrule 27. The end of the ferrule 27 opposite from an emission end face 23b of the optical fiber 23 for illumination is joined to a support 28 so that the ferrule 27 is supported at one end by the support 28 to allow oscillation. The optical fiber 23 for illumination extends through the support 28.

The ferrule 27 is, for example, made of a metal such as nickel. The ferrule 27 may be formed in any shape, such as a quadrangular prism or a cylinder. Piezoelectric elements 30x and 30y are mounted on the ferrule 27 by adhesive or the like to oppose each other in the x-direction and the y-direction, where the x-direction and y-direction are orthogonal to each other in a plane orthogonal to the z-direction, and the z-direction is a direction parallel to the optical axis direction of the optical fiber 23 for illumination. Only one of the piezoelectric elements 30x is illustrated in FIG. 3. The piezoelectric elements 30x and 30y are rectangular, with the long sides in the z-direction. The piezoelectric elements 30x and 30y each have an electrode formed on both surfaces in the thickness direction and are each configured to be capable of expanding and contracting in the z-direction upon voltage being applied in the thickness direction via the opposing electrodes.

Corresponding wiring cables 31 are connected to the electrode surfaces of the piezoelectric elements 30x and 30y opposite the electrode surfaces adhered to the ferrule 27. Similarly, corresponding wiring cables 31 are connected to the ferrule 27, which acts as a common electrode for the piezoelectric elements 30x and 30y. To the two piezoelectric elements 30x opposite each other in the x-direction, in-phase AC voltage is applied from the apparatus body 40 through the corresponding wiring cables 31. Similarly, to the two piezoelectric elements 30y opposite each other in the y-direction, in-phase AC voltage is applied from the apparatus body 40 through the corresponding wiring cables 31.

With this configuration, when one of the two piezoelectric elements 30x expands, the other contracts, causing the ferrule 27 to vibrate by bending in the x-direction. Similarly, when one of the two piezoelectric elements 30y expands, the other contracts, causing the ferrule 27 to vibrate by bending in the y-direction. As a result, the x-direction vibration and y-direction vibration are combined, so that the ferrule 27 is deflected integrally with the emission end 23a of the optical fiber 23 for illumination. Accordingly, upon illumination light entering the optical fiber 23 for illumination from the apparatus body 40, an object being observed (object being illuminated) 32 can be scanned in 2D by the illumination light emitted from the emission end face 23b.

The fiber bundle 24 for detection is disposed to pass through the peripheral portion of the insertion part 22. A non-illustrated detection lens may also be disposed at the tip 24a of each fiber in the fiber bundle 24 for detection. While the scope 20 is connected to the apparatus body 40, the object being observed 32 is irradiated by illumination light, and the fiber bundle 24 for detection captures light that is reflected, scattered, or refracted by the object being observed 32 (light that interacts with the object being observed 32), fluorescent light generated by irradiation with the illumination light, or other light as signal light and guides the signal light to the apparatus body 40.

The example of the illumination optical system 26 in FIG. 3 is configured by two projection lenses 26a, 26b. The projection lenses 26a, 26b are configured so as to concentrate illumination light, emitted from the emission end face 23b of the optical fiber 23 for illumination, on a predetermined focal position. The illumination optical system 26 is not limited to two projection lenses 26a, 26b and may be configured as a single lens or as three or more lenses.

In this embodiment, the scope 20 further includes a memory 35, as illustrated in FIG. 1. The memory 35 stores information on optical characteristics related to the chromatic aberration of magnification of the illumination optical system 26 with respect to light of a plurality of predetermined colors, such as red (R), green (G), and blue (B). The stored information on optical characteristics may, for example, be information expressed as a third order or higher polynomial equation or a trigonometric function, or an expansion or conversion formula of these, representing the relationship between the amount of deflection (image height) h of the illumination light and the scanning angle θλ of light of each color relative to the optical axis of the illumination optical system 26. While the scope 20 is connected to the apparatus body 40, the apparatus body 40 reads the information on optical characteristics stored in the memory 35.

In FIG. 1, the apparatus body 40 includes a controller 41 that controls the entire scanning endoscope apparatus 10, a light source 42, a drive controller 43, an optical detector 44, a scanning pattern calculator 45, an image processor 46, and a memory 47.

The light source 42 includes lasers 51R, 51G, 51B and a multiplexer 52. Under control by the controller 41, the laser 51R emits red laser light, the laser 51G emits green laser light, and the laser 51B emits blue laser light. For example, Diode-Pumped Solid-State (DPSS) lasers or laser diodes may be used as the lasers 51R, 51G, and 51B. The wavelength of each color light may, for example, be from 440 nm to 460 nm for blue, 515 nm to 532 nm for green, and 635 nm to 638 nm for red. The laser light emitted from the lasers 51R, 51G, and 51B is combined on the same axis by the multiplexer 52 and is incident on the optical fiber 23 for illumination of the scope 20. The light source 42 may include a different plurality of light sources. The light source 42 may also be stored in a housing that is separate from the apparatus body 40 and is connected to the apparatus body 40 by a signal wire. In this case, the optical fiber 23 for illumination of the scope 20 is detachably connected to the housing that includes the light source 42.

The drive controller 43 supplies a required drive signal to the actuator 25 of the scope 20 through the wiring cables 31 and subjects the emission end of the optical fiber 23 for illumination to vibration driving. For example, the drive controller 43 repeatedly supplies drive signals that gradually increase and decrease in amplitude to the piezoelectric elements 30$x$ and 30$y$ of the actuator 25. The drive signals differ in phase by nearly 90° and are at or near the resonance frequency of the vibrated portion, which includes the emission end 23$a$ of the optical fiber 23 for illumination. As a result, the emission end face 23$b$ of the optical fiber 23 for illumination is displaced in a spiral shape centered on the optical axis of the illumination optical system 26, and the object being observed 32 is scanned in a spiral shape by the illumination light emitted from the emission end face 23$b$.

The optical detector 44 includes a spectrometer 55, photodetectors (PDs) 56R, 56G, 56B, and Analog-Digital Converters (ADCs) 57R, 57G, 57W While the scope 20 is connected to the apparatus body 40, the spectrometer 55 is coupled to the fiber bundle 24 for detection of the scope 20, and signal light guided by the fiber bundle 24 for detection is split for example into the colors R, G, B. The PDs 56R, 56G, 56B detect the light of the corresponding color split by the spectrometer 55 and subject the light to photoelectric conversion. The PDs 56R, 56G, 56B then output analog pixel signals, which the corresponding ADCs 57R, 57G, 57B convert to digital pixel signals and output to the image processor 46.

While the scope 20 is connected to the apparatus body 40, the scanning pattern calculator 45 reads the information on optical characteristics of the illumination optical system 26 from the memory 35. With reference to the information on optical characteristics read from the memory 35 and to drive signal information, such as the amplitude and phase of the drive signal driving the actuator 25, the scanning pattern calculator 45 calculates the scanning pattern (coordinates), on the object being observed 32, of light of each of the colors R, G, B. The drive signal information is, for example, acquired from the controller 41 or the drive controller 43. FIG. 1 illustrates the case of acquiring the drive signal information from the controller 41. The scanning pattern calculator 45 provides the calculated scanning pattern of light of each color to the image processor 46.

By referring to the scanning pattern of light of each of the colors R, G, B as calculated by the scanning pattern calculator 45, the image processor 46 stores the pixel signal of each color acquired from the ADCs 57R, 57G, 57B, for example at the corresponding plot position of a frame memory. The image processor 46 then performs necessary image processing, such as interpolation, during or after the completion of scanning of each frame, generates images of sequential frames of the object being observed 32, and displays the images on the display 60.

The memory 47 stores information such as control programs of the apparatus body 40. The memory 47 may also function as a working memory for the scanning pattern calculator 45 and the image processor 46.

Next, the information on optical characteristics that is related to the chromatic aberration of magnification of the illumination optical system 26 and is stored in the memory 35 of the scope 20 is described.

Figure 4:
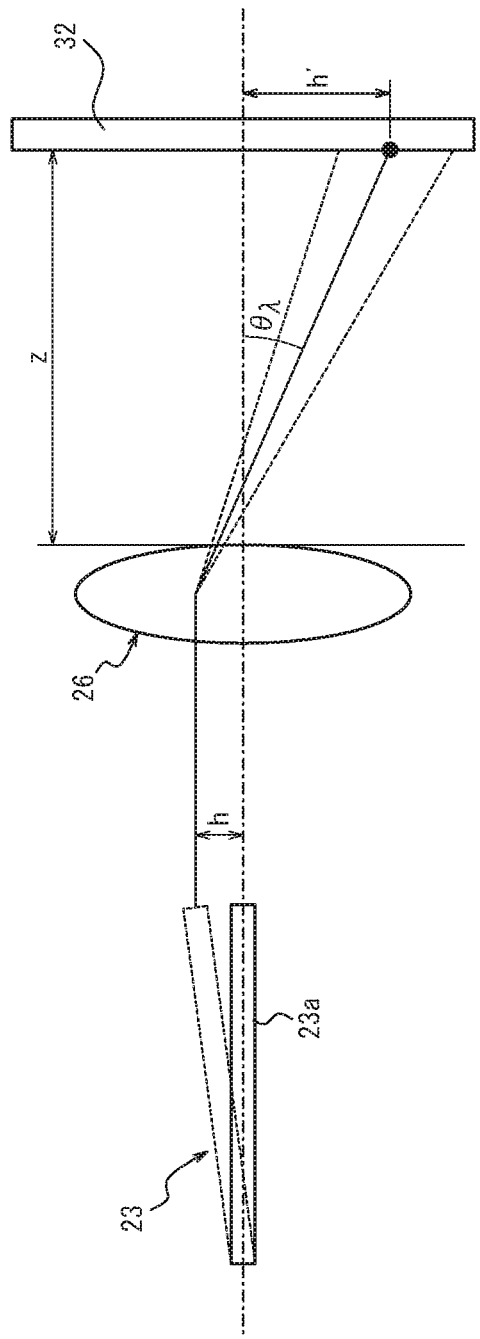
FIG. 4 schematically illustrates the chromatic aberration of magnification of the illumination optical system.
Figure 5:
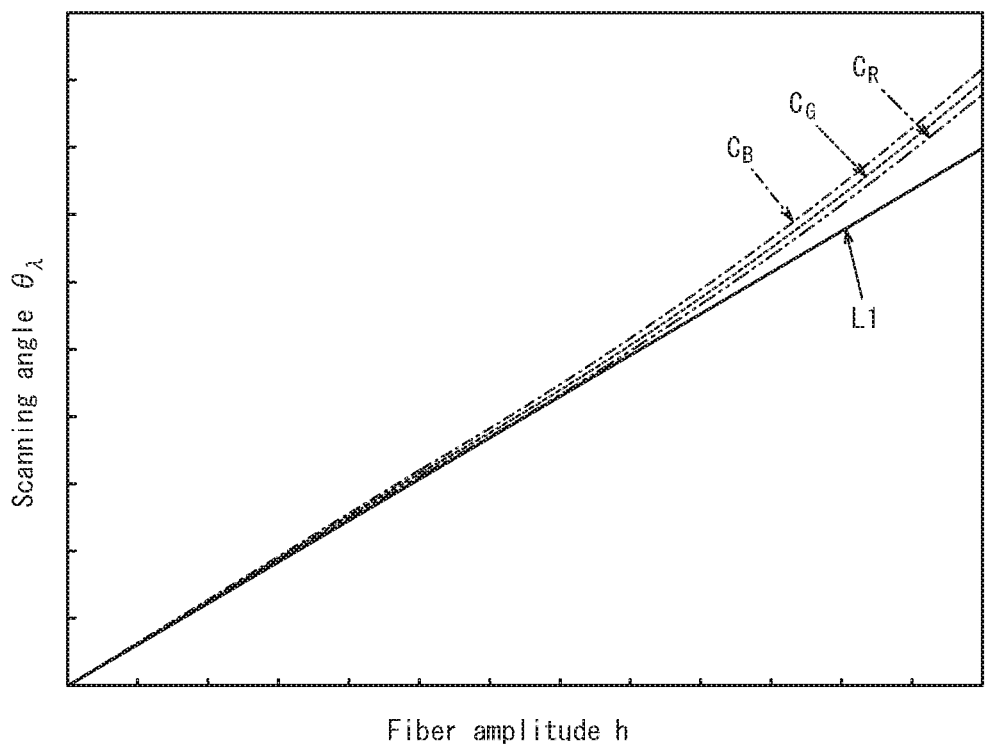
FIG. 5 illustrates an example of the chromatic aberration of magnification of the illumination optical system.

As illustrated schematically in FIG. 4, the emission end 23$a$ of the optical fiber 23 for illumination is displaced, and illumination light is deflected from the optical axis of the illumination optical system 26 and enters the illumination optical system 26. The illumination light passing through the illumination optical system 26 then irradiates different positions on the object being observed 32 for light of each color as a result of the chromatic aberration of magnification of the illumination optical system 26. For example, let h be the amount of deflection (fiber amplitude) from the optical axis of incident light and θλ be the angle between the optical axis and the light of each of the colors R, G, B passing through the illumination optical system 26 (scanning angle). Upon illumination light of wavelengths R, G, B entering the illumination optical system 26, the scanning angle θλ of light of each color for example changes as illustrated in FIG. 5 in accordance with an increase in the fiber amplitude h. In an ideal case with no chromatic aberration of magnification, the scanning angle θλ of light of each color increases linearly at the same angle in accordance with an increase in the fiber amplitude h, as indicated by the characteristic L1. By contrast, chromatic aberration of magnification causes the scanning angle θλ of light of each color to increase over a curve at different angles in accordance with an increase in the fiber amplitude h, as indicated by the characteristics $C_R$, $C_G$, and $C_B$.

In the case of the illumination optical system 26 having chromatic aberration of magnification such as in FIG. 5, the characteristics $C_R$, $C_G$, $C_B$ can be expressed for example as the fourth order polynomial $h = a_4 \theta \lambda^4 + a_3 \theta \lambda^3 + a_2 \theta \lambda^2 + a_1 \theta \lambda^1 + a_0$, where $a_4$, $a_3$, $a_2$, $a_1$, and $a_0$ coefficients, or $\theta \lambda = b_4 h^4 + b_3 h^3 + b_2 h^2 + b_1 h + b_0$, where $b_4$, $b_3$, $b_2$, $b_1$, and $b_0$ are coefficients, using the fiber amplitude h and the scanning angle θλ.

Figure 6:
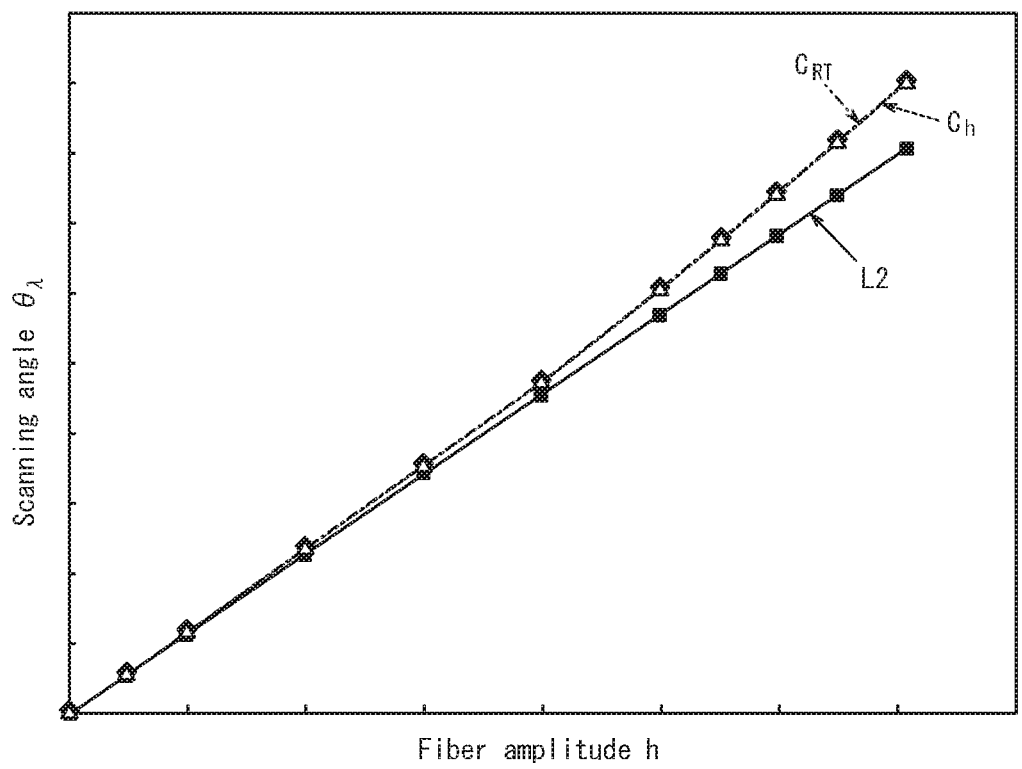
FIG. 6 illustrates the chromatic aberration of magnification of the illumination optical system using principal ray tracing.

With principal ray tracing, the scanning angle θλ of light of each color due to the chromatic aberration of magnification of the illumination optical system 26 changes in accordance with an increase in the fiber amplitude h as illustrated in FIG. 6, for example. Specifically, as indicated by the characteristic L2, the scanning angle θλ increases linearly in accordance with an increase in the fiber amplitude h with paraxial approximation. By contrast, as indicated by the characteristic $C_{RT}$, the scanning angle θλ increases along a curve in accordance with an increase in the fiber amplitude h with principal ray tracing. In this case, the characteristic $C_{RT}$ can be approximated by the curve $C_h$ expressed for example as the trigonometric function h=f·sin θλ, where the focal length of the illumination optical system 26 is f.

Hence, the information stored in the memory 35 of the scope 20 as the information on optical characteristics related to the chromatic aberration of magnification of the illumination optical system 26 may, for example, be $h=a_4\theta\lambda^4+a_3\theta\lambda^3+a_2\theta\lambda^2+a_1\theta\lambda^1+a_0$ or $\theta\lambda=b_4h^4+b_3h^3+b_2h^2+b_1h+b_0$, or may be h=f·sin θλ. If h=f·sin θλ is stored in the memory 35, the focal length f is preferably an actual measured value. Storing such a value achieves highly accurate correction of the chromatic aberration of magnification of the illumination optical system 26 by allowing for individual variation between illumination optical systems 26. Note that the illumination optical system 26 is simplified in FIG. 4.

Next, the image display method by the scanning endoscope apparatus 10 of FIG. 1 is described.

Figure 7:
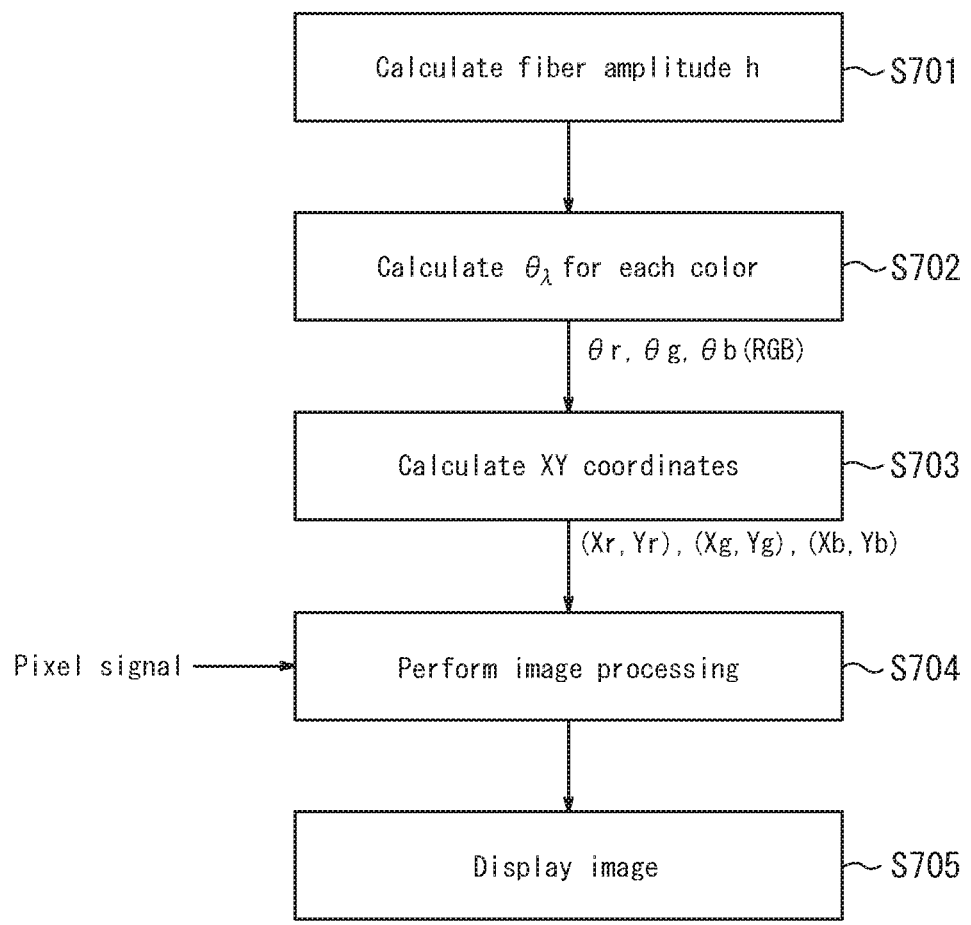
FIG. 7 is a flowchart illustrating the main processing in the image display method by the scanning endoscope apparatus of FIG. 1.

FIG. 7 is a flowchart illustrating the main processing in the image display method. The processing in FIG. 7 is executed under the control of the controller 41. First, with reference to the drive signal information of the actuator 25, the scanning pattern calculator 45 calculates the fiber amplitude h corresponding to each sequential scanning point during the scanning period of each frame (step S701). Each scanning point for example is the timing at which the amplitude of the x-direction drive signal and the y-direction drive signal reaches a peak. The peak value differs for each scanning point.

Next, the scanning pattern calculator 45 calculates the scanning angles $\theta_R$, $\theta_G$, $\theta_B$ for the light of each of the colors R, G, B by referring to the information on optical characteristics read from the memory 35 of the scope 20 and the calculated fiber amplitude h (step S702). Subsequently, the scanning pattern calculator 45 calculates the coordinates $(X_R, Y_R)$, $(X_G, Y_G)$, $(X_B, Y_B)$ of the scanning point (irradiation position) of the light of each color on the object being observed 32 by referring to the calculated scanning angles $\theta_R$, $\theta_G$, $\theta_B$ for the light of each color (step S703).

As illustrated in FIG. 4, the distance hλ' is expressed as hλ'=z·tan θλ, where z is the object distance from the illumination optical system 26 to the object being observed 32 and hλ' (λ: R, G, B) is the distance from the optical axis of the illumination optical system 26 to the incident position of light of each color on the object being observed 32. In step S703, the scanning pattern calculator 45 calculates the distance hλ' and then calculates the coordinates $(X_R, Y_R)$, $(X_G, Y_G)$, $(X_B, Y_B)$ of the light of each color by referring to the calculated distance hλ'. The scanning pattern calculator 45 thus calculates the coordinates of sequential scanning points on the object being observed 32 for light of each of the colors R, G, B, i.e. calculates the scanning pattern, and provides the result to the image processor 46. The object distance z may be stored in the memory 35 of the scope 20 and read along with the information on optical characteristics or may be stored in and read from the memory 47 of the apparatus body 40.

The scanning pattern calculator 45 may perform the above-described calculation of the scanning pattern of light of each color while the actuator 25 is driven or without the actuator 25 being driven. In the former case, the scanning pattern calculator 45 may perform the calculation while the object being observed 32 is actually being scanned by being irradiated with illumination light or before actual scanning, without the object being observed 32 being irradiated with illumination light.

Subsequently, by referring to the scanning pattern (coordinates) of light of each of the colors R, G, B as calculated by the scanning pattern calculator 45, the image processor 46 stores the pixel signal of each color acquired, by scanning the object being observed 32, from the ADCs 57R, 57G, 57B for example at the corresponding plot position of the frame memory. The image processor 46 then performs necessary image processing, such as interpolation, and generates an image of the object being observed 32 (step S704). This image of the object being observed generated by the image processor 46 is displayed on the display 60 (step S705).

Only the blue portion of the illumination light irradiated onto the object being observed 32 is present at the outermost periphery of the scanning area due to the chromatic aberration of magnification of the illumination optical system 26. At this outermost periphery of the scanning area, processes such as interpolation cannot be performed sufficiently, which may lead to a color shift. In this embodiment, different image processing than in other areas is preferably performed on the scanning area that is further out than the area scanned by red illumination light, i.e. the outermost area of the image of the object being observed 32 displayed on the display 60. Such other image processing may include trimming, monochrome conversion, or pseudocolor conversion. With this approach, the image of the object being observed 32 at the periphery can be clearly recognized as a different image, thereby preventing the image of the object being observed 32 from suffering color shift and improving the overall quality of displayed images.

In general, it is troublesome to acquire coordinate information of the scanning pattern using the light irradiation coordinate detection module, such as a PSD. According to this embodiment, the chromatic aberration of magnification of the illumination optical system 26 can be corrected easily, without using a light irradiation coordinate detection module such as a PSD.

This disclosure is not limited to the above embodiments, and a variety of changes or modifications may be made. For example, the information on optical characteristics stored in the memory 35 of the scope 20 and relating to the chromatic aberration of magnification of the illumination optical system 26 is not limited to the above examples. This information may be expressed as a third order or higher polynomial equation or a trigonometric function, or an expansion or conversion formula of these. The actuator 25 is not limited to a piezoelectric method and may instead adopt another known driving method, such as a MEMS mirror or an electromagnetic method that uses coils and a permanent magnet. In the above embodiments, the case of scanning by simultaneously irradiating light of the colors R, G, B on the object being observed 32 has been described. Alternatively, light of each color may be irradiated and images displayed by a frame sequential method, or light of each color may be irradiated sequentially within one scan, with an image then being displayed.

The memory 35 of the scope 20 may store an ID that can identify the type of the illumination optical system 26 in the scope 20, and the memory 47 of the apparatus body 40 may store information on optical characteristics corresponding to a plurality of types of illumination optical systems 26. In this case, the controller 41 of the apparatus body 40 may read the ID of the illumination optical system 26 from the memory 35 of the connected scope 20 and output the corresponding information on optical characteristics from the memory 47 to the scanning pattern calculator 45. A portion or the entirety of the drive controller 43, optical detector 44, scanning pattern calculator 45, image processor 46, and memory 47 may be included in the controller 41. Furthermore, this disclosure is not limited to a scanning endoscope apparatus and may also be adopted in a scanning microscope that scans a sample through an objective lens by deflecting laser light.

REFERENCE SIGNS LIST

10 Scanning endoscope apparatus
20 Scope
23 Optical fiber for illumination
23a Emission end
24 Fiber bundle for detection
25 Actuator
26 Illumination optical system
30x, 30y Piezoelectric element
32 Object being observed (object being illuminated)
35 Memory
40 Apparatus body
41 Controller
42 Light source
43 Drive controller
44 Optical detector
45 Scanning pattern calculator
46 Image processor
47 Memory
60 Display

The invention claimed is:

1. A scanning observation apparatus that deflects illumination light with an actuator through an illumination optical system to scan an object being illuminated, subjects light from the object being illuminated to photoelectric conversion with an optical detector, performs processing with one or more controllers, and displays an image of the object being illuminated on a display, the scanning observation apparatus comprising:
a memory configured to store information on optical characteristics related to a chromatic aberration of magnification of the illumination optical system relative to light of a plurality of predetermined colors;
the one or more controllers being configured to:
calculate a scanning pattern, on the object being illuminated, of the light of each color by referring to the information on optical characteristics;
by referring to the scanning pattern, calibrate a plot position yielded by a photoelectric conversion signal from the optical detector for the light of each color and generate an image of the object being illuminated;
wherein as the information on optical characteristics, the memory stores information expressed as a third order or higher polynomial equation or a trigonometric function, or an expansion or conversion formula of the polynomial equation or the trigonometric function, representing a relationship between an amount of deflection h of the illumination light and a scanning angle $\theta\lambda$ of the light of each color relative to an optical axis of the illumination optical system, and
for the light of each color, the one or more controllers calculates an irradiation position h' serving as the scanning pattern from the equation $h'=z \cdot \tan \theta\lambda$ by referring to the information on optical characteristics, where z is a distance from the illumination optical system to the object being illuminated.

2. The scanning observation apparatus of claim 1, wherein as the information on optical characteristics, the memory stores information expressed as $h=a_4\theta\lambda^4+a_3\theta\lambda^3+a_2\theta\lambda^2+a_1\theta\lambda+a_0$, where $a_4$, $a_3$, $a_2$, $a_1$, and $a_0$ are coefficients, or $\theta\lambda=b_4h^4+b_3h^3+b_2h^2+b_1h+b_0$, where $b_4$, $b_3$, $b_2$, $b_1$, and $b_0$ are coefficients.

3. The scanning observation apparatus of claim 1, wherein as the information on optical characteristics, the memory stores information expressed as $h=f \cdot \sin \theta\lambda$, where f is a focal length of the illumination optical system.

4. The scanning observation apparatus of claim 3, wherein the focal length f is an actual measured value.

5. The scanning observation apparatus of claim 1, wherein
the object being illuminated is scanned in a spiral centered on an optical axis of the illumination optical system; and
the one or more controllers performs different image processing on an outermost area of the image of the object being illuminated than on another area.

6. The scanning observation apparatus of claim 1, further comprising:
an optical fiber configured to guide the illumination light; wherein
the actuator displaces an emission end of the optical fiber to deflect the illumination light emitted from the optical fiber.

7. An image display method of a scanning observation apparatus that deflects illumination light with an actuator through an illumination optical system to scan an object being illuminated, subjects light from the object being illuminated to photoelectric conversion with an optical detector, performs processing with one or more controllers, and displays an image of the object being illuminated on a display, the image display method comprising:
calculating, using one or more controllers, a scanning pattern on the object being illuminated by referring to information on optical characteristics stored in a memory and related to a chromatic aberration of magnification of the illumination optical system relative to light of a plurality of predetermined colors, the scanning pattern being calculated for the light of each color; and
calibrating, using the one or more controllers, a plot position by referring to the scanning pattern, the plot position being yielded by a photoelectric conversion signal from the optical detector for the light of each color, and generating an image of the object being illuminated;
wherein as the information on optical characteristics, the memory stores information expressed as a third order or higher polynomial equation or a trigonometric function, or an expansion or conversion formula of the polynomial equation or the trigonometric function, representing a relationship between an amount of deflection h of the illumination light and a scanning angle $\theta\lambda$ of the light of each color relative to an optical axis of the illumination optical system, and
for the light of each color, the one or more controllers calculates an irradiation position h' serving as the scanning pattern from the equation $h'=z \cdot \tan \theta\lambda$ by referring to the information on optical characteristics, where z is a distance from the illumination optical system to the object being illuminated.

* * * * *